US00PP10052P

United States Patent [19]

Glicenstein

[11] Patent Number: Plant 10,052

[45] Date of Patent: Oct. 7, 1997

[54] CHRYSANTHEMUM PLANT NAMED 'ROSE SERENADE'

[75] Inventor: Leon Glicenstein, Salinas, Calif.

[73] Assignee: Yoder Brothers, Inc., Barberton, Ohio

[21] Appl. No.: 605,618

[22] Filed: Feb. 22, 1996

[51] Int. Cl.[6] ..... A01N 5/00

[52] U.S. Cl. ..... Plt./76

[58] Field of Search ..... Plt./76, 81

[56] References Cited

U.S. PATENT DOCUMENTS

| | | | |
|---|---|---|---|
| P.P. 8,782 | 6/1994 | Fuess | Plt./76 |
| P.P. 8,803 | 6/1994 | Fuess | Plt./76 |
| 4,616,099 | 10/1986 | Sparkes | 47/58 |

OTHER PUBLICATIONS

Broertjes, et al. 1980, "A mutant of a mutant of a . . . Irradiation of progressive radiation–induced mutants in a mutation breeding programme with *Chrysanthemum morifolium*", Euphytica, 29:525–530.

Gosling, ed., 1979, "The Chrysanthemum Manual–6th edition", the National Chrysanthemum Society, Essex Telegraph Press, Ltd., London, pp. 329–336.

Broertjes, et al., 1978, "Application of Mutation Breeding Methods in the Improvement of Vegetatively Propagated Crops", Elsevier Sci. Pub. Co., New York, pp. 162–175.

Searle, et al., 1968, "Chrysanthemums the Year Round", Blanford Press, London, pp. 27–29, 320–327.

Chan, 1966, "Chrysanthemum and rose mutations induced by x–rays", Am. Soc. Hort. Sci. Proc., pp. 613–620.

Broetjes, 1966, "Mutation breeding of Chrysanthemums", Euphytica, 15:156–162.

Dowrick, et al., 1966, "The induction of mutations in Chrysanthemum using x–and gamma radiation", Eyphytica, 15:204–210.

*Primary Examiner*—Howard J. Locker

*Attorney, Agent, or Firm*—Foley & Lardner

[57] ABSTRACT

A Chrysanthemum plant named Rose Serenade particularly characterized by its flat capitulum form; decorative capitulum type; red-purple ray floret color; diameter across face of capitulum of 51 to 64 mm when fully opened; branching pattern is spreading and prolific, with 8 laterals developing after pinch when grown outside under natural daylength in fall flowerings; natural season flower date of August 22 to 27 when planting rooted cuttings on June 17 to 21 in Salinas, Calif., and of September 22 to 25 when planting rooted cuttings June 15 to 18 in Hightstown, N.J.; plant height of 28 to 36 cm when grown in fall under natural daylength with no growth regulators; and durable, uniform performance.

1 Drawing Sheet

The present invention comprises a new and distinct cultivar of Chrysanthemum, botanically known as *Dendranthema grandiflora*, and referred to by the cultivar name Rose Serenade.

Rose Serenade, identified as 9634 (89-#02EO9), is a product of a mutation induction program. The new cultivar was discovered and selected by inventor Leon Glicenstein on Jul. 20, 1993 in a controlled environment in Salinas, Calif. as one flowering plant within a flowering block established as rooted cuttings from stock plants which had been exposed as unrooted cuttings to an X-ray source of 1750 rads in Fort Myers, Fla. on May 10, 1993. The irradiated parent cultivar was the cultivar Empire Serenade, disclosed in U.S. Plant Pat. No. 8,803 and described as a flat decorative garden mum with red- purple to greyed-purple flower color.

The irradiation program resulting in Rose Serenade had as its primary objective the expansion of color ranges of the cultivar Empire Serenade. The irradiation program comprised irradiation of cuttings of the parent cultivar at irradiation levels of 1500, 1750 and 2000 rads. A total of 430 cuttings harvested from a total of 225 irradiated plants were planted on May 10, 1993. Of these, 17 initial selections were made, which selections were then revegetated and reflowered. Three consecutive flowerings resulted in discarding 7 selections on Apr. 8, 1994. Two selections died in the revegetation process. The 8 remaining selections were maintained as PIs (Possible Introductions) and were further trialed in Salinas, Calif., Hightstown, N.J. and Leamington, Ontario, Canada, ultimately resulting in the decision to discard 5 selections on Oct. 17, 1994, and to introduce one selection as Rose Serenade. Two remaining selections were trialed further, and ultimately discarded on Oct. 13, 1995.

The first act of asexual reproduction of Rose Serenade was accomplished when vegetative cuttings were taken from the initial selection in September of 1993 in a controlled environment in Salinas, Calif., by technicians working under supervision of Leon Glicenstein.

Horticultural examination of controlled flowerings of successive plantings has shown that the unique combination of characteristics as herein disclosed for Rose Serenade are firmly fixed and are retained through successive generations of asexual reproduction.

Rose Serenade has not been observed under all possible environmental conditions. The phenotype may vary significantly with variations in environment such as temperature, light intensity and daylength, without, however, any variance in genotype.

The following observations, measurements and comparisons describe plants grown in controlled open areas in Salinas, Calif., and in Hightstown, N.J. Rooted cuttings were established in soil and maintained outdoors under the natural temperature and daylength prevailing during June through October.

The following traits have been repeatedly observed and are determined to be basic characteristics of Rose Serenade, which, in combination, distinguish this Chrysanthemum as a new and distinct cultivar:

1. Flat capitulum form.
2. Decorative capitulum type.
3. Red-purple ray floret color.
4. Diameter across face of capitulum of 51 to 64 mm when fully opened.
5. Branching pattern is spreading and prolific, with 8 laterals developing after pinch when grown outside under natural daylength in fall flowerings.
6. Natural season flower date of August 22 to 27 when planting rooted cuttings on June 17 to 21 in Salinas, Calif., and of September 22 to 25 when planting rooted cuttings June 15 to 18 in Hightstown, N.J.

7. Plant height of 28 to 36 cm when grown in fall under natural daylength with no growth regulators.

8. Durable, uniform performance.

The accompanying photographic drawing is a color photograph of Rose Serenade grown as a pinched garden mum under natural season outside conditions in Salinas, Calif., with the colors being as nearly true as possible with illustrations of this type. Plants were grown outside and dug and transplanted in 15 cm pots for photography purposes.

Of the commercial cultivars known to the inventor, the most similar in comparison to Rose Serenade is the parent cultivar Empire Serenade. All traits of Rose Serenade are similar to those of Serenade, except for the ray floret color. The ray floret color of Rose Serenade is a different shade of red-purple (R.H.S. 64A to 64B) than the red-purple to greyed-purple color (R.H.S. between 59C and 186B) of Empire Serenade.

In the following description color references are made to The Royal Horticultural Society Colour Chart. The color values were determined on plant material grown as a pinched garden mum grown outdoors in Salinas, Calif. on Aug. 21, 1995.

Classification:

*Botanical.*—*Dendranthema grandiflora* cv Rose Serenade.

*Commercial.*—Flat decorative garden mum.

Inflorescence

A. Capitulum:

*Form.*—Flat

*Type.*—Decorative.

*Diameter across face.*—51 to 64 mm when fully opened.

B. Corolla of ray florets:

*Color (general tonality from a distance of three meters).*—Red-purple.

*Color (upper surface).*—64A to 64B.

*Color (under surface).*—4D, tip overlaid with 64A.

*Shape .*—Cross-section convex, longitudinal section of outer ray florets slightly convex. Ray floret tips rounded.

*Color (mature).*—6B.

*Color (immature).*—6B, tinged with 151D.

D. Reproductive organs:

*Androecium.*—Present on disc florets only; scant pollen.

*Gynoecium.*—Present on both ray and disc florets.

Plant

A. General Appearance:

*Height.*—28 to 36 cm when grown in fall under natural daylength with no growth regulators.

*Branching pattern.*—spreading and prolific, with 8 laterals developing after pinch when grown outside under natural daylength in fall flowerings.

B. Foliage:

*Color (upper surface).*—147A.

*Color (under surface).*—147B.

*Shape.*—Small, lobed, slightly serrated.

What is claimed is:

1. A new and distinct Chrysanthemum plant named Rose Serenade, as described and illustrated.

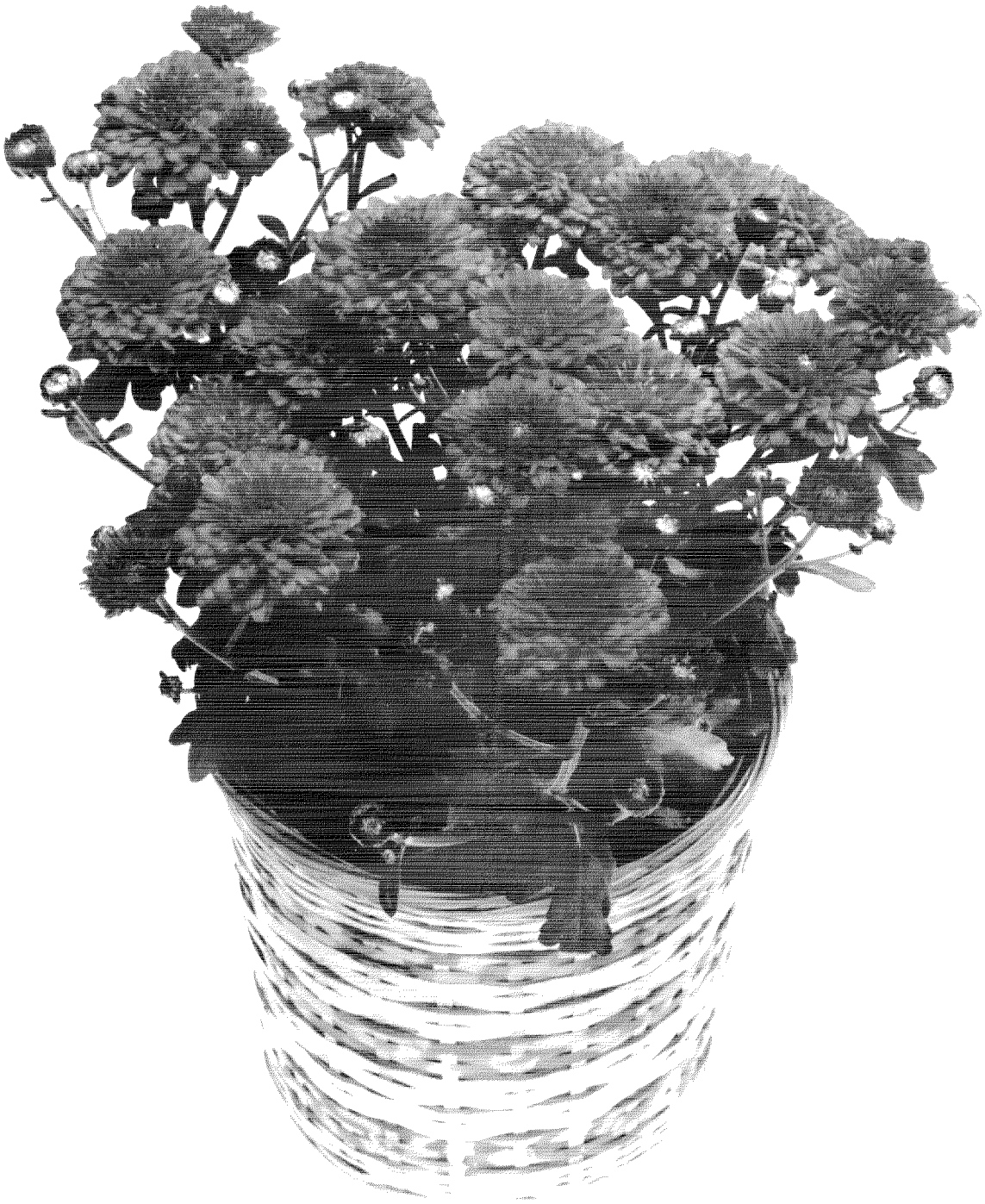

* * * * *